US011198890B2

(12) United States Patent
Liao et al.

(10) Patent No.: US 11,198,890 B2
(45) Date of Patent: Dec. 14, 2021

(54) PREPARATION OF (R)-3-HYDROXYBUTYRIC ACID OR ITS SALTS BY ONE-STEP FERMENTATION

(71) Applicant: NNB Nutrition USA, LLC, Frisco, TX (US)

(72) Inventors: Kylin Liao, Nanjing (CN); Wenchao Fan, Nanjing (CN)

(73) Assignee: NNB Nutrition USA, LLC, Frisco, TX (US)

( * ) Notice: Subject to any disclaimer, the term of this patent is extended or adjusted under 35 U.S.C. 154(b) by 0 days.

(21) Appl. No.: 16/542,044

(22) Filed: Aug. 15, 2019

(65) Prior Publication Data

US 2019/0376098 A1 Dec. 12, 2019

Related U.S. Application Data

(62) Division of application No. 15/944,331, filed on Apr. 3, 2018, now Pat. No. 10,428,357.

(60) Provisional application No. 62/481,476, filed on Apr. 4, 2017.

(51) Int. Cl.
| | |
|---|---|
| *C12P 7/42* | (2006.01) |
| *C12R 1/15* | (2006.01) |
| *C12N 1/20* | (2006.01) |
| *C07C 53/124* | (2006.01) |
| *C12N 9/04* | (2006.01) |
| *C12N 9/10* | (2006.01) |

(52) U.S. Cl.
CPC .............. *C12P 7/42* (2013.01); *C07C 53/124* (2013.01); *C12N 1/20* (2013.01); *C12N 1/205* (2021.05); *C12N 9/0006* (2013.01); *C12N 9/1029* (2013.01); *C12N 9/13* (2013.01); *C12R 2001/15* (2021.05)

(58) Field of Classification Search
CPC ....... C12P 7/42; C12N 9/0006; C12N 9/1029; C12N 9/13; C12N 1/20; C12R 1/15; C07C 53/124
See application file for complete search history.

(56) References Cited

U.S. PATENT DOCUMENTS

| | | | |
|---|---|---|---|
| 6,696,561 B1 | 2/2004 | Pompejus et al. | |
| 7,132,267 B2 | 11/2006 | Davis et al. | |
| 7,148,051 B2 | 12/2006 | Payne et al. | |
| 2003/0203459 A1 | 10/2003 | Chen et al. | |
| 2006/0280721 A1* | 12/2006 | Veech | ..................... C07C 51/09 424/78.37 |
| 2014/0363847 A1 | 12/2014 | Fujii et al. | |
| 2017/0258745 A1* | 9/2017 | Millet | .................. A61K 31/198 |

FOREIGN PATENT DOCUMENTS

| | | |
|---|---|---|
| CN | 107083406 A | 8/2017 |
| WO | 2002100530 A2 | 12/2002 |
| WO | 2014190251 | 11/2014 |
| WO | WO 2017/016902 * | 2/2017 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Jo et al., Journal of Bioscience and Engineering 104(6):457-463, 2007.*
Kikuchi et al., Applied and Environmental Microbiology 69(1):358-366, 2003.*
Tokiwa et al., Journal of Biotechnology 132:264-272, 2007.*
Söhling et al., Journal of Bacteriology 178(3):871-880, 1996.*
Yuan et al., Microbial Cell Factories 18:46, pp. 1-11; 2019.*
PubChem, "(R)-3-Hydroxybutyric acid," Oct. 4, 2015, https://pubchem.ncbi.nlm.nih.gov/compound/_R_-3-Hydroxybutyric_acid.
NCBI "3-hydroxybutyrate dehydrogenase [Corynebacterium glutamicum]," Jan. 16, 2014, https://www.ncbi.nlm.nih.gov/protein/KIH72748.1?report=gpwithparts&log$=seqview.

* cited by examiner

*Primary Examiner* — Delia M Ramirez
(74) *Attorney, Agent, or Firm* — Weisun Rao; Jun Chen; Venture Partner, LLC

(57) ABSTRACT

The subject invention relates to a process of preparing (R)-3-hydroxybutyric acid or a salt thereof by one-step fermentation with a nonpathogenic microorganism. The fermentation of (R)-3-hydroxybutyric acid was performed by supplying with certain carbon and nitrogen sources. These microorganisms include a Glutamic acid Bacterium HR057 strain or one type of genetically engineered *Corynebacterium Glutamicum*.

6 Claims, No Drawings

PREPARATION OF (R)-3-HYDROXYBUTYRIC ACID OR ITS SALTS BY ONE-STEP FERMENTATION

CROSS-REFERENCE TO RELATED APPLICATIONS

This application is a divisional application of U.S. application Ser. No. 15/944,331, now U.S. Pat. No. 10,428,357, filed on Apr. 3, 2018, which claims priority to U.S. Application No. 62/481,476, filed on Apr. 4, 2017, the contents of which are incorporated herein by reference in their entirety.

TECHNICAL FIELD OF THE INVENTION

The subject invention pertains to the field of bioengineering, in particular to a process for preparing (R)-3-hydroxybutyric acid and its salts by microbial fermentation.

BACKGROUND OF THE INVENTION (R)-3-hydroxybutyrate (3-HB) is an optically chiral compound with the CAS No. 625-72-9. (R)-3-hydroxybutyric acid is produced by the metabolism of long chain fatty acids in the liver of mammals. It exists as a major ketone in plasma and peripheral tissues and can be used as an energy source in most tissues of the body.

(R)-3-hydroxybutyric acid has positive effect on treating many diseases and nutritional functions as well. For example, it can be used to treat many diseases that arise from elevated levels of ketone (such as nerve disorders including epilepsy and myoclonus, and neurodegenerative diseases including Alzheimer's disease and dementia); it can reduce free radical damage by oxidizing the coenzyme Q (such as ischemia); it can enhance the efficiency of metabolism to achieve the treatment of inadequate support, angina, myocardial infarction, etc. by improving training efficiency and athletic performance; it can also be used to treat cancer related diseases such as brain cancer (astrocytoma, etc.). Further, it has good effects on the treatment of glucose metabolism disorders (such as type-1 diabetes, type-2 diabetes, hypoglycemia ketone disease, etc.). It can be used to control osteopenia (osteopenia), osteoporosis, severe osteoporosis and related fractures. Based on these functions and therapeutic and nutritional effects, (R)-3-hydroxybutyric acid and its salts can be used as food additives and drugs with great health and medicinal values.

(R)-3-hydroxybutyric acid has been prepared primarily by chemical methods. It can be made from direct chemical synthesis or prepared by enzymatic degradation of poly-3-hydroxybutyrate with poly-3-hydroxybutyric acid depolymerase. The chemical synthesis of (R)-3-hydroxybutyric acid requires a high temperature, a high pressure and expensive chiral metal catalysts. The process of enzymatic degradation of poly-3-hydroxybutyric acid requires a large amount of organic solvent, and very pure poly-3-hydroxybutyrate as starting material. Besides the long reaction time, it is difficult to control the racemization of product after reaction. Moreover, this method needs more optimization in the laboratory to meet even higher requirements for industrial scale commercialization because of high cost and low efficiency.

At present, most of the commercially available 3-hydroxybutyric acid is a racemic mixture, with the ratio of (R)-3-hydroxybutyric acid to (S)-3-hydroxybutyric acid being about one to one. Although study showed that (S)-3-hydroxybutyric acid is not physiologically active, racemic 3-hydroxybutyric acid and its salts, especially sodium salts, are still the main commodity form and accepted by most consumers. It is expected that a single optical (R)-3-hydroxybutyric acid and its salts will become popular in future, replacing the racemic 3-hydroxybutyric acid and its salts.

Generally, it is believed that natural or biological compounds are safer (and non-toxic) than chemically produced compounds. People prefer the "natural" or "biological" feature of the source of pharmaceutical, food and cosmetic ingredients. For marketing purpose, pharmaceuticals, food, and cosmetics manufacturers are more willing to replace chemical process with biological process for making the same product. Therefore, there has been a goal to produce (R)-3-hydroxybutyric acid in a biological method instead of a chemical method which is the main method.

BRIEF SUMMARY OF THE INVENTION

In order to produce "safe and nontoxic" (R)-3-hydroxybutyric acid in a biological method, inventors have studied various biological methods and unexpectedly found that fermentation procedures by nonpathogenic microorganism as the host were able to produce (R)-3-hydroxybutyric acid in an unusually efficient one-step process. Optimally engineered organisms have been screened and selected by genetic engineering technology to enhance the expression of genes associated with (R)-3-hydroxybutyric acid main metabolic pathway and weaken the branched metabolic pathway. After that, (R)-3-hydroxybutyric acid can be effectively accumulated in the fermentation process, which has broad application prospect in industrial scale.

Accordingly, in one aspect, this invention provides a biological process for efficiently producing (R)-3-hydroxybutyric acid (e.g., in a one-step method). In another aspect, this invention provides a food grade (R)-3-hydroxybutyric acid and salts thereof. In still another aspect, this invention also provides food grade racemic 3-hydroxybutyric acid and its salts to meet the needs of the market. In yet still another aspect, this invention further provides a bacterium which can ferment a fermentation medium to produce (R)-3-hydroxybutyric acid.

Specifically, one aspect of the present invention provides a process for producing (R)-3-hydroxybutyric acid comprising fermenting a fermentation broth with a nonpathogenic microorganism. In this process, the fermentation broth comprises carbon and nitrogen sources and an enzyme that is overexpressed by the nonpathogenic microorganism, the carbon and nitrogen sources are directly converted into (R)-3-hydroxybutyric acid by one-step fermentation with the nonpathogenic microorganism, the (R)-3-hydroxybutyric acid was recovered from fermentation broth after it was excreted during fermentation, the nonpathogenic microorganism is selected from a group consisting of *Corynebacterium glutamicum, Bacillus subtilis, Brevibacterium* lactofermentum, *Brevibacterium difficile, Brevibacterium flavum* and *Brevibacterium breve*; and the nonpathogenic microorganism has the following biotransformation capability: converting pyruvic acid and coenzyme A to acetyl-CoA, converting acetyl-CoA into acetoacetyl-CoA, converting acetoacetyl-CoA to acetoacetic acid, and converting acetoacetic acid to (R)-3-hydroxybutyric acid.

In some embodiments, the enzyme overexpressed by the nonpathogenic microorganism comprises a member selected from the group consisting of succinyl-CoA transferase, acetoacetyl-CoA synthase, and 3-HB dehydrogenase. In some prefer embodiments, the microorganism overexpresses succinyl-CoA transferase and 3-HB dehydrogenase.

In some embodiments, the nonpathogenic microorganism comprises *Corynebacterium glutamicum*, Glutamic acid Bacterium HR057, *Bacillus subtilis, Brevibacterium* lactofermentum, *Brevibacterium difficile, Brevibacterium flavum*, or *Brevibacterium breve*. In some preferred embodiments, the microorganism comprises *Corynebacterium glutamicum* or Glutamic acid Bacterium HR057. In some more preferred embodiments, the microorganism is *Corynebacterium glutamicum* (such as that deposited at the China General Microbiological Culture Collection Center under the accession number CGMCC No. 13111).

In some embodiments, the carbon source comprises a member selected from the group consisting of glucose, sucrose, maltose, molasses, starch and glycerol. In some other embodiments, the nitrogen source comprises a member selected from the group consisting of an organic nitrogen source and an inorganic nitrogen source. Examples of suitable organic nitrogen source include, but are not limited to, corn steep liquor, bran hydrolyzate, soybean cake hydrolyzate, yeast extract, yeast powder, peptone, and urea; wherein Examples of suitable inorganic nitrogen source include, but are not limited to, ammonium sulfate, ammonium nitrate, and aqueous ammonia.

In some embodiments, the (R)-3-hydroxybutyric acid produced by the process of this invention is free of bacterial endotoxin and has a purity of 95% or more.

In some embodiments, the (R)-3-hydroxybutyric acid prepared by the process of this invention is in the form of (R)-3-hydroxybutyrate sodium salt, (R)-3-hydroxybutyrate potassium salt, (R)-3-hydroxybutyrate magnesium salt, or (R)-3-hydroxybutyrate calcium salt.

Another aspect of this invention provides a racemic 3-hydroxybutyric acid prepared by racemization treatment of the (R)-3-hydroxybutyric acid or a (R)-3-hydroxybutyrate salt produced in accordance of the process of this invention.

Another aspect of this invention provides a nonpathogenic microorganism which is selected from the group consisting of *Corynebacterium glutamicum*, Glutamic acid Bacterium HR057, *Bacillus subtilis, Brevibacterium* lactofermentum, *Brevibacterium difficile, Brevibacterium flavum*, and *Brevibacterium breve*.

In some embodiments, the nonpathogenic microorganism is a *Corynebacterium glutamicum* strain or a Glutamicacid Bacterium HR057 strain. For instance, the *Corynebacterium glutamicum* strain is as deposited at the China General Microbiological Culture Collection Center under the accession number CGMCC No. 13111.

In some preferred embodiments, the nonpathogenic microorganism is capable of producing (R)-3-hydroxybutyric acid in a one-step fermentation process of this invention.

The invention comprises the following technical scheme:

Fermentation of (R)-3-hydroxybutyric acid is carried out by using a non-pathogenic microorganism, which directly converts the carbon and nitrogen sources into (R)-3-hydroxybutyric acid which is excreted into the fermentation broth and could be recovered directly. The microorganism can be one or more members selected from the group consisting of *Corynebacterium glutamicum, Bacillus subtilis, Brevibacterium* lactofermentum, *Brevibacterium difficile, Brevibacterium flavum* and *Brevibacterium breve*. These microorganisms have the following biotransformation functions: converting pyruvic acid and coenzyme A to acetyl-CoA; converting acetyl-CoA into acetoacetyl-CoA; converting acetoacetyl-CoA to acetoacetic acid; and then converting acetoacetic acid to (R)-3-hydroxybutyric acid.

Preferably, the microorganism over-expresses one or more enzymes selected from the group consisting of succinyl-CoA transferase, acetoacetyl-CoA synthase, and 3-HB dehydrogenase (3-HB Dehydrogenase, BDH).

More preferably, the microorganism overexpresses succinyl-CoA transferase or 3-HB dehydrogenase.

Preferably, the microorganism inhibits or down regulates the expression of β-ketothiolase.

In a preferred embodiment, the microorganism is *Corynebacterium glutamicum*.

In another preferred embodiment, the *Corynebacterium glutamicum* is as deposited at the China General Microbiological Culture Collection Center under the accession number CGMCC No. 13111.

Different media may be used for different microorganisms in the fermentation process. The carbon source may be selected from the group consisting of glucose, sucrose, maltose, molasses, starch and glycerol. One or more organic or inorganic nitrogen sources may be used in a fermentation medium. The organic nitrogen source may come from the group consisting of corn steep liquor, bran hydrolyzate, soybean cake hydrolyzate, yeast extract, yeast meal, peptone and urea; and the inorganic nitrogen source may include one or more compounds selected from the groups consisting of ammonium sulfate, ammonium nitrate, and aqueous ammonia.

In a preferred embodiment of the present invention, the fermentation medium includes glucose 75 g/L, corn steep liquor 25-30 g/L, $(NH_4)_2SO_4$ 20 g/L, $KH_2PO_4$ 1.5 g/L, $MgSO_4 \cdot 7H_2O$ 0.5 g/L, urea 1.0 g/L, histidine 30 mg/L, molasses 25 g/L, biotin 100 μg/L, and defoamer 0.2 g/L when *Corynebacterium glutamicum* was applied.

Preferably, the feed medium includes ammonium sulfate 500 g/L and glucose 650 g/L when batch feed fermentation was performed.

The purity of the (R)-3-hydroxybutyric acid prepared by a fermentation method of the present invention could be greater than 95%, greater than 96%, greater than 97%, greater than 98%, or even greater than 99%.

Pure (R)-3-hydroxybutyric acid thus prepared does not contain bacterial endotoxin and chemical odor such as bitterness.

(R)-3-hydroxybutyric acid is an acid which forms a salt with a base. Alternatively, the (R)-3-hydroxybutyric acid prepared by present invention may exist in the form of a salt, such as sodium salt, potassium salt, magnesium salt, or calcium salt, preferably in the form of a sodium salt. These salts may all be optically active compounds.

Since racemic 3-hydroxybutyric acid and its sodium salt have traditionally been accepted by food and pharmaceutical manufacturers and consumers, (R)-3-hydroxybutyric acid and its salts can be subjected to racemic treatment to prepare racemic 3-hydroxybutyric acid and its salts. For example, racemization can be achieved by heating (R)-3-hydroxybutyric acid in an alkaline solution such as sodium hydroxide solution for a certain time.

The racemic 3-hydroxybutyrate salt may be sodium 3-hydroxybutyrate, potassium 3-hydroxybutyrate, magnesium 3-hydroxybutyrate, or calcium 3-hydroxybutyrate.

(R)-3-hydroxybutyric acid and its salts prepared by the present invention are free of bacterial endotoxin and toxic chemicals, therefore ensuring food safety. In addition, (R)-3-hydroxybutyric acid can be used directly to manufacture pharmaceuticals and health products as it contains no chemical residues or chemical reaction impurities, and it does not have chemical odor such as bitterness as well.

The genetically engineered microorganisms constructed in the present invention can effectively produce and accumulate (R)-3-hydroxybutyric acid in the fermentation broth during the fermentation process, and could give rise to food-grade (R) level by downstream process, which has broad industrial prospects.

Corynebacterium glutamicum has been engineered to produce (R)-3-hydroxybutyric acid at high yield. A strain of this microorganism has been deposited under the accession number CGMCC No. 13111 on Oct. 14, 2016, at China General Microbiological Culture Collection Center, located in Institution of Microbiology, Chinese Academy of Sciences, Building 3, No. 1 Beicheng West Road, Chaoyang District, Beijing, China 100101.

As used herein, the term "one-step fermentation" refers to a fermentation process that includes adding one or more fermenting agents (e.g., a microorganism) to a fermentation medium which is fermented to give the desired product, without having to add a second round of fermenting agent and then going through a second round of fermentation process.

As used herein, the term "nonpathogenic microorganism" refers to a microorganism that generally does not cause disease, harm or death to another microorganism, an organism, or human being.

DETAILED DESCRIPTION OF THE INVENTION

The present invention is further described in detail with specific embodiments. The following examples are intended to demonstrate the invention and not to limit the scope of the invention.

Mass percentage is referred in the invention such as the added amount, content and concentration of multiple substances unless otherwise provided described or defined.

In the embodiments provided under the present invention, room temperature (15-30° C.) is referred to by default unless otherwise provided described or specified.

In the present invention, a microorganism strain capable of producing (R)-3-hydroxybutyric acid by fermentation is exemplified by but not limited to "Corynebacterium glutamicum", "Corynebacterium glutamicum strain CGMCC No. 13111", or "Glutamic acid Bacterium HR057".

Fermentation of (R)-3-hydroxybutyric acid by microorganism was investigated in the present invention in order to supply the consumer and pharmaceutical and food manufacturers with the "naturalized" or "biogenic" sources of (R)-3-hydroxybutyric acid and its salts, 3-hydroxybutyric acid and its salts.

The inventors screened and selected species for the construction of genetic engineering strains. It is not considered that general strain with potentially pathogenic feature such as Escherichia coli. Nonpathogenic microorganism was chosen and genetically engineered as fermentation strains such as Corynebacterium glutamicum, Bacillus subtilis, Brevibacterium lactofermentum, Brevibacterium difficile, Brevibacterium breve and Brevibacterium brevica. Several strains were obtained through screening which are able to produce (R)-3-hydroxybutyric acid by fermentation. No endotoxin was produced at all during fermentation, which may cause harm to most people. So, it is considered as non-toxic and harmless" design.

It is necessary to adjust and control some parameters such as dissolved oxygen, temperature, pH etc., to have a higher yield of (R)-3-hydroxybutyric acid during fermentation.

The constant dO2 is controlled at 15% to 25% during fermentation. Fermentation can be carried out under the following conditions: air flow is about 1 vvm, where vvm is the ratio of the amount of ventilation per minute to the actual volume of liquid in the tank (for example, 1 vvm is equal to 30 L/min for a fermenter containing 30 liters of fermentation broth, and 1 vvm is equal to 5 L/min as for a fermentation tank containing 5 liters of fermentation broth,).

Preferably, the temperature is first controlled at 30~32° C. during the initial stage of fermentation and then increased to 34~37° C. at the later stage of the fermentation which facilitates the synthesis and excretion of (R)-3-hydroxybutyric acid by the microorganism.

The pH is generally controlled at pH 6.0~8.0, preferably at pH 6.5~7.0, during the initial stage of fermentation. It can then be adjusted to 6.8~7.0 in the later stages of fermentation to facilitate the synthesis and drainage of (R)-3-hydroxybutyric acid from the fermentation broth.

The above term "later stage of fermentation" refers to from exponential stage to stationary stage of microbial growth. For example, the OD600 nm value is no longer rising and tending to decrease when monitoring cell density with OD600 nm values.

The residual sugar is controlled at 1.0%~3.0% during fermentation process, more precisely at 1.5%~2.5%.

After the fermentation is completed, the fermentation broth needs to be recovered and (R)-3-hydroxybutyric acid is extracted therefrom. For example, the supernatant of the fermentation broth is obtained by centrifugation. The supernatant is concentrated if necessary; (R)-3-hydroxybutyric acid is separated by a post-treatment such as purification and drying.

Cells and macromolecules in the fermentation medium can be removed by filtration (including ultrafiltration, nanofiltration, etc.). Concentrated filtration, and other post-processing means such as drying, purification and other methods may be applied if necessary to isolate (R)-3-hydroxybutyric acid. Alternatively, (R)-3-hydroxybutyric acid can be isolated by centrifugation which obtains supernatant of fermentation broth, then go through ultrafiltration, nanofiltration and other methods to remove macromolecules, or through concentrated filtration if necessary, then by drying, purification and other post-processing means.

To prepare (R)-3-hydroxybutyrate such as sodium salt, potassium salt, magnesium salt, calcium salt, an equivalent amount of (R)-3-hydroxybutyric acid is reacted with the corresponding base or metal oxide such as sodium hydroxide. The reaction temperature is controlled to be 30° C. or lower, preferably at 25° C. or lower, and more preferably at 20° C. or less, where the racemic reaction could be avoided as much as possible.

As the whole preparation process does not require or involve an organic solvent, chemical odor like bitterness was not detected from the product (R)-3-hydroxybutyric acid which could be directly used to manufacture pharmaceuticals and health care products.

EXAMPLE 1

Pre-Culture and Fermentation

A glycerol stock CGMCC No. 13111 stored at −80° C. was thawed and inoculated to a 5000 mL flask containing 500 mL seed medium (75 g/L of glucose, 25-30 g/L of corn steep liquor, 20 g/L of $(NH_4)_2SO_4$, 1.5 g/L of $KH_2PO_4$, 0.5 g/L of $MgSO_4 \cdot 7H_2O$, 1.0 g/L of urea, 30 mg/L of histidine, 25 g/L of molasses, 100 μg/L of biotin, pH 7.0), and cultured at 30° C. for 18 hours. The seed culture cultivation was completed when OD=0.4-0.5.

500 mL seed culture was inoculated into a 7-liter fermenter filled with 5 liters medium. The composition of fermentation medium was the same as the seed medium described above, and the pH was controlled at 6.4~6.7 after sterilization. Feed medium contains 500 g/L ammonium sulfate and 650 g/L glucose. The fermentation temperature was set at 30° C., the tank pressure was kept at 0.05 Mpa, and the initial ventilation ratio was 1 vvm. Stirring speed was 600 rpm. The pH of the fermentation was about pH 6.5.

The pH was controlled at 6.7 and the temperature was raised to 35° C. at the later phase of fermentation. The dissolved oxygen constant (dO2) was controlled at 15~25% by adjusting ventilation and stirring speed. To control residual sugar level, sugar was fed slowly while the concentration of the original sugar dropped to about 3.0% and the residual sugar was controlled at 1.5%~2.0%. (R)-3-hydroxybutyric acid was accumulated to 11.8 g/L after 72 hours.

EXAMPLE 2

Isolation of Fermentation Broth and Extraction of (R)-3-hydroxybutyric Acid 5.2 liters of the fermentation broth obtained in Example 1 was centrifuged at 4500 rpm and the cells were discarded. The supernatant was filtered with 1% diatomaceous earth. Clear filtrate was recovered after stirring for 30 minutes mixed with 1% activated carbon.

The filtrate was concentrated through nanofiltration membrane, and the resulting filtrate was passed through a 732 cation exchange resin to get a 1000 g/L concentrated filtrate. The concentrated collection was oily and collected while hot to give 56.8 g of (R)-3-hydroxybutyric acid with a yield of 92.5%. The purity of (R)-3-hydroxybutyric acid was determined by high performance liquid chromatography. The chromatographic column was Shim-pack Vp-ODSC18 column (150 L×4.6). The mobile phase consisted of acetonitrile: water (v/v)=15: 85, UV detection wavelength was 210 nm, injection volume was 20 μL, flow rate was 1 mL/min, column temperature was 10° C. The purity of (R)-3-hydroxybutyric acid was 98% and the specific optical value was [α] D20=−25° (C=6%, H$_2$O).

EXAMPLE 3

Preparation of Sodium (R)-3-hydroxybutyrate

A neutralization reaction was performed by mixing 5 g of (R)-3-hydroxybutyric acid obtained in Example 2 with an equivalent amount of a 2.0 N sodium hydroxide solution at 25° C. or lower. 4.9 g of sodium (R)-3-hydroxybutyrate powder was finally obtained with an 81% yield by rotating concentration, standing for 2 hours, and being collected by suction filtration and dried at 60° C. The salt has a melting point of 152° C. and a specific optical value [α] D20 of −14.1° (C=10%, H2O).

EXAMPLE 4

Racemization of (R)-3-hydroxybutyric Acid 10 g of (R)-3-hydroxybutyric acid was slowly added to 100 mL of a 2.0 N sodium hydroxide solution, and the mixture was heated to 60° C. for 4 hours. The optical value of product was 0° at room temperature. A neutralization reaction was carried out by adding hydrochloric acid to adjust the pH of the mixture to 7.0. 10.3 g of sodium 3-hydroxybutyrate powder was obtained with a yield of 85% by rotary evaporation until a solid was observed, allowing to stand for 2 hours, and then filtration. The results showed that racemic 3-hydroxybutyrate was obtained.

In summary, the present invention disclosed that the engineered *Corynebacterium glutaricum* by genetic modification could ferment (R)-3-hydroxybutyric acid in a one-step process at a high yield, which was proved to be safe and non-toxic food grade. The engineered strain and manufacturing process that were disclosed in this invention has broad industrial application prospects.

What is claimed is:

1. A process for producing (R)-3-hydroxybutyric acid, wherein the process comprises culturing *Corynebacterium glutamicum* strain deposited under the accession number CGMCC No. 13111 at the China General Microbiological Culture Collection Center in a fermentation broth, wherein the fermentation broth comprises carbon and nitrogen sources, and the carbon and nitrogen sources are directly converted into (R)-3-hydroxybutyric acid by a one-step fermentation, wherein the (R)-3-hydroxybutyric acid is recovered from the fermentation broth after it is excreted during fermentation.

2. The process of claim 1, wherein the carbon source is selected from the group consisting of glucose, sucrose, maltose, molasses, starch and glycerol.

3. The process of claim 1, wherein the nitrogen source is selected from the group consisting of an organic nitrogen source and an inorganic nitrogen source.

4. The process of claim 3, wherein the organic nitrogen source is selected from the group consisting of corn steep liquor, bran hydrolysate, soybean cake hydrolysate, yeast extract, yeast powder, peptone, and urea.

5. The process of claim 3, wherein the inorganic nitrogen source is selected from the group consisting of ammonium sulfate, ammonium nitrate, and aqueous ammonia.

6. The process of claim 1, wherein the (R)-3-hydroxybutyric acid is prepared in the form of (R)-3-hydroxybutyrate sodium salt, (R)-3-hydroxybutyrate potassium salt, (R)-3-hydroxybutyrate magnesium salt, or (R)-3-hydroxybutyrate calcium salt.

* * * * *